United States Patent [19]
Beane

[11] Patent Number: 5,133,714
[45] Date of Patent: Jul. 28, 1992

[54] ELECTROSURGICAL SUCTION COAGULATOR

[75] Inventor: Richard M. Beane, Hingham, Mass.

[73] Assignee: Kirwan Surgical Products, Inc., Rockland, Mass.

[21] Appl. No.: 696,143

[22] Filed: May 6, 1991

[51] Int. Cl.$^5$ .............................................. A61B 17/36
[52] U.S. Cl. ............................................ 606/49; 606/35
[58] Field of Search ................................... 606/27-29, 606/37-42, 45, 49; 604/21, 22, 35, 45; 128/752

[56] References Cited

U.S. PATENT DOCUMENTS

| | | | |
|---|---|---|---|
| 3,902,494 | 9/1975 | Haberlen et al. | 606/49 |
| 3,974,833 | 8/1976 | Durden, III | 606/49 |
| 4,096,864 | 6/1978 | Kletschka et al. | 604/35 |
| 4,356,823 | 11/1982 | Jackson | 604/35 |
| 4,932,952 | 6/1990 | Wojciechowicz, Jr. | 606/49 |

Primary Examiner—Peter A. Aschenbrenner

[57] ABSTRACT

The invention disclosed herein is directed at a suction coagulator having a contact wire and a suction tube which has a portion thereof circumscribed by an insulating layer. The suction tube is electrically conductive and electrically connected to the contact wire and portions of both the contact wire and the suction tube, with its insulating layer, have a layer of plastic material molded thereabout to form a first insert. The first insert includes a body section having a surface through which a vent extends and an airway is formed within the first insert in spaced parallel relation with the upper surface of the first insert and in communication with the vent. A vent activation button is integrally formed from the upper surface of the body section and a longitudinally extending baffle forms the lower wall of the airway.

4 Claims, 2 Drawing Sheets

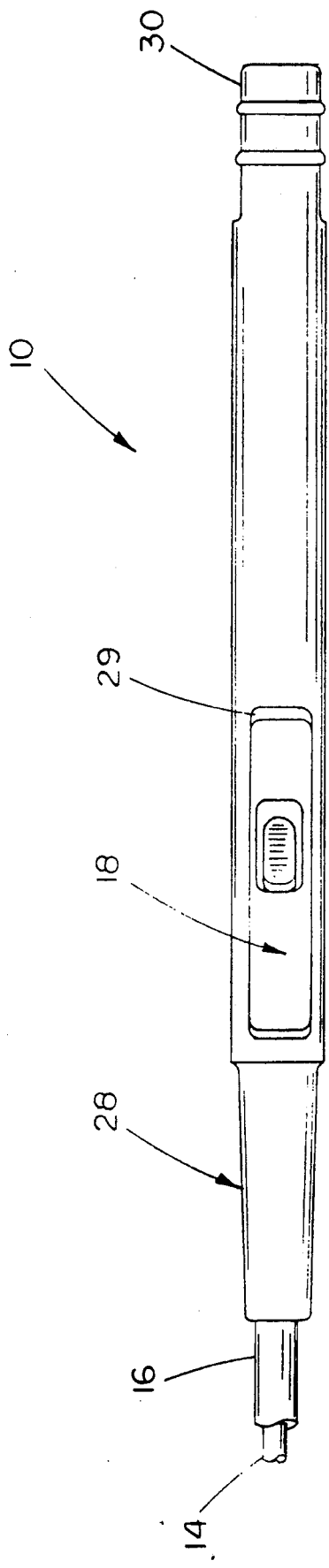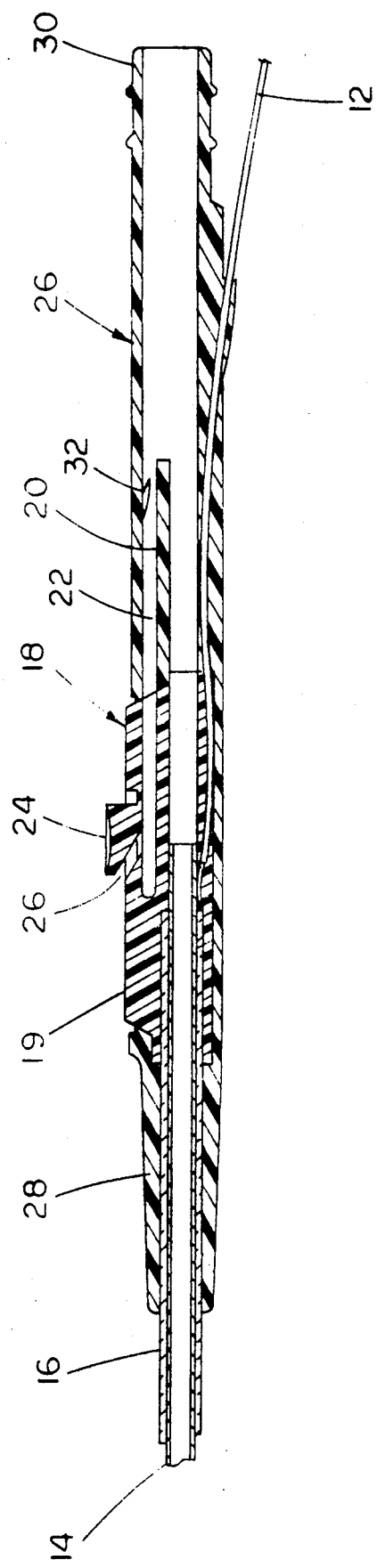

ELECTROSURGICAL SUCTION COAGULATOR

BACKGROUND OF THE INVENTION

Field of the Invention

This invention relates to surgical instruments and more specifically to electrosurgical suction coagulators.

SUMMARY OF THE INVENTION

The invention disclosed herein is directed at a suction coagulator having a contact wire and a suction tube which has a portion thereof circumscribed by an insulating layer. The suction tube is electrically conductive and electrically connected to the contact wire and portions of both the contact wire and the suction tube, with its insulating layer, have a layer of plastic material molded thereabout to form a first insert. The first insert includes a body section having a surface through which a vent extends and an airway is formed within the first insert in spaced parallel relation with the upper surface of the first insert and in communication with the vent. A vent activation button is integrally formed from the upper surface of the body section and a longitudinally extending baffle forms the lower wall of the airway.

BRIEF DESCRIPTION OF THE DRAWINGS

Further details are explained below with the help of the example(s) illustrated in the attached drawings in which:

FIG. 1 is a top plan view of the suction coagulatora rotary switch according to the present invention;

FIG. 2 is a section taken along the longitudinal midline of FIG. 1;

DESCRIPTION OF THE PREFERRED EMBODIMENT(S)

Figure 3:
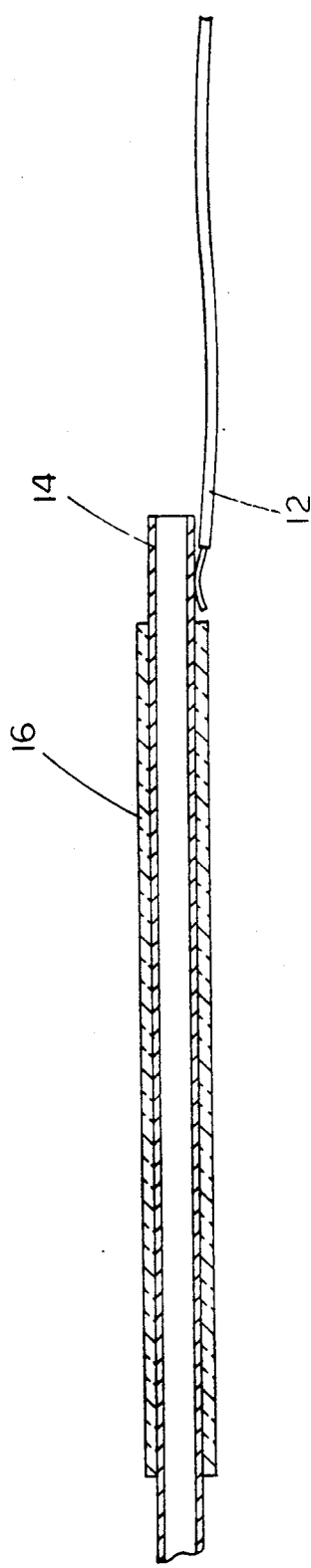
FIG. 3 is a sectional view of the subassembly of the insulating layer, suction tube and the contact wire of the suction coagulator shown in FIG. 1.
Figure 4:
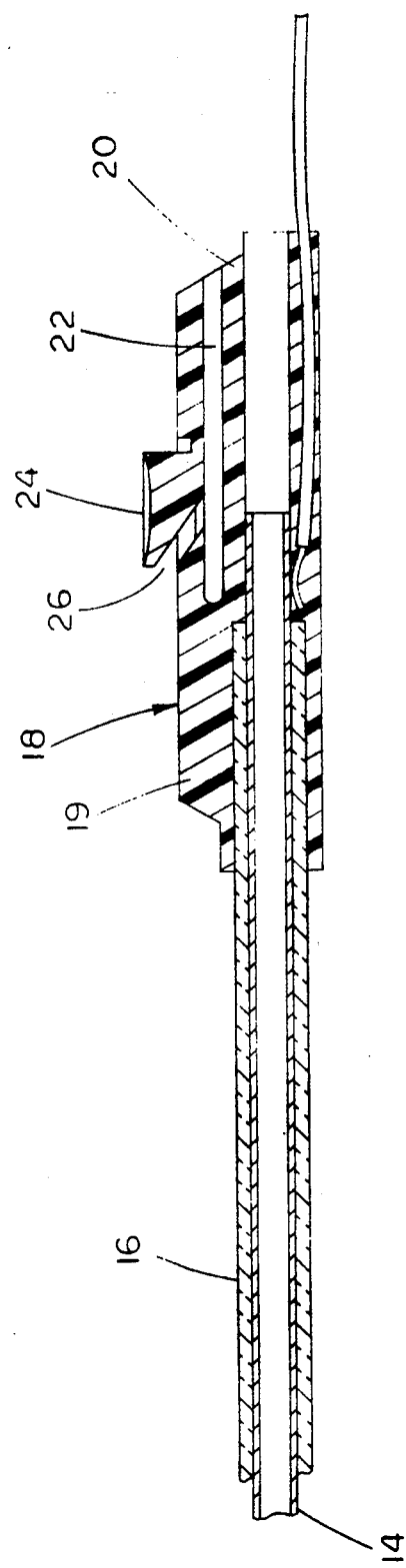
FIG. 4 is a sectional view of the first insert of the suction coagulator shown in FIG. 1.

There is shown in the drawings a suction coagulator 10 comprising a contact wire 12 and a suction tube 14. A portion of the external surface of the suction tube 14 is circumscribed by an insulating layer 16. The suction tube 14 is formed of a electrically conductive material, metal for example, which is electrically connected to the contact wire 12 and portions of both the contact wire 12 and the suction tube 14, with its insulating layer 16, have a layer of plastic material molded there about to form a body portion 28. A first insert is formed of plastic material and the first insert 18 includes a body section 19 having an upper surface through which a vent 26 extends. An airway 22 is formed within the first insert 18 in spaced parallel relation with the upper surface of the first insert 18 and in communication with the vent 26. A vent activation button 24 is formed from the upper surface of the body section 19 and a longitudinally extending baffle 20 provides the lower wall of the airway 22 all as shown in FIGS. 2 and 4. The vent activation button 24 provides a positive barrier between fluid in the airway 22 and the surgeon's hand.

The body portion 28 includes an aperture 29 whose edges are in abutting relation to the periphery or common surfaces of the first insert 18 as shown most clearly in FIG. 4. The material from which the body portion 28 is formed will fuse with the material from which the body section 19 is formed providing a seal. The body portion 28 also provides a continuation of the airway 22 and the baffle 20 as shown in FIG. 2. The free terminal end 30 of the body portion 28 is formed to provide a means of connection with the vacuum line in the operating theatre (not shown). A one-way duckbill check valve 32 is positioned in the airway 22 of the body portion 28, permitting suction to be applied when the vent 26 is open while preventing fluids from entering the airway 22. If the surgeon presses the vent activation button 24 closing the vent 26 and simultaneously activates the electrical circuit coagulation will take place when the instrument is used. If the vent is open, suction may be applied removing debris and fluids from the operating site out through the free terminal end 30 of the body portion 28 to a refuse site. Suction is applied continuously during the use of the coagulator.)

The combination of the contact wire 12 whose bare end is attached by soldering, for example, to the exterior of the suction tube 14 provides the electrical path which supplies the coagulation circuit. The other end of the contact wire 12 from that attached to the suction tube 14 is connected to a generator and foot switch (neither of which is shown) which supplies the power. The coagulation circuit has at its other end remote from the generator means of engaging bipolar forceps, for example.

In old constructions, conductive liquid moving up the suction tube 14 would have access to a vent. Should the surgeon, being electrically grounded, have his finger on the vent when he activates the generator, he will become part of the electrical circuit and may be seriously injured. The construction disclosed herein due to the use of the body section 19 and the use of a body portion 28 which provides an extra long baffle 20 creates a longer pathway for the stray fluid to flow thereby reduces the amount of such stray fluid. The use of the vent activation button 24 provides a physical barrier between the surgeon and any current carrying fluid which may have found its way into the airway 22 and the use of the one-way duckbill check valve 32 further prevents any current carrying fluid from getting into vent 26 through the airway 22.

What I claim is:

1. A electrosurgical suction coagulator comprising a contact wire, a body portion, a first insert, and a suction tube, the suction tube having a portion, the portion of the suction tube circumscribed by an insulating layer, the suction tube is electrically conductive and electrically connected to the contact wire and portions of both the contact wire and the suction tube, with its insulating layer, have a layer of plastic material molded thereabout to form the body portion, the first insert includes a body section, a body section upper surface, a vent, and an airway, the vent extending through the body section upper surface and the airway formed within the first insert, in spaced parallel relation with the body section upper surface of the first insert and in communication with the vent, the body portion having an body portion upper surface, the body portion upper surface having an aperture formed therethrough, the first insert mounted in the aperture, the airway communicating with the body portion.

2. An electrosurgical suction coagulator as set forth in claim 1, further comprising a vent activation button integrally formed from and hingedly associated with the body section upper surface and a longitudinally extending baffle forming the lower wall of the airway.

3. An electrosurgical suction coagulator as set forth in claim 2 wherein a major portion of the airway is forward of the vent activation button.

4. An electrosurgical suction coagulator as set forth in claim 2 wherein a one-way valve is positioned in the airway of the body section whereby the valve prevent a flow from the body portion to the vent.

* * * * *